United States Patent [19]
Nakamura et al.

[11] Patent Number: 6,027,467
[45] Date of Patent: Feb. 22, 2000

[54] CERVICAL ORTHOSIS

[75] Inventors: Toshiro Nakamura, Oda; Hidenaga Kawai, Yunotsu-cho, both of Japan

[73] Assignee: Nakamura Brace Co., Ltd., Oda, Japan

[21] Appl. No.: 09/247,477

[22] Filed: Feb. 9, 1999

[30] Foreign Application Priority Data

Feb. 9, 1998 [JP] Japan .................. 10-044337

[51] Int. Cl.$^7$ .................................................. A61F 5/00
[52] U.S. Cl. .................................... 602/18; 128/DIG. 23
[58] Field of Search ................... 602/5, 17, 18; 128/DIG. 23

[56] References Cited

U.S. PATENT DOCUMENTS

| | | | |
|---|---|---|---|
| 3,164,151 | 1/1965 | Nicoll . | |
| 3,916,885 | 11/1975 | Gaylord | ..................... 602/18 |
| 4,702,233 | 10/1987 | Omicioli . | |
| 4,881,529 | 11/1989 | Santos . | |

FOREIGN PATENT DOCUMENTS 39 02 434   8/1990   Germany .

*Primary Examiner*—Michael A. Brown
*Attorney, Agent, or Firm*—Armstrong, Westerman, Hattori, McLeland & Naughton

[57] ABSTRACT

A cervical orthosis to be wound onto the neck of user around the cervical vertebrae part and retained to support and fix the cervical vertebrae wherein almost the whole of at least the surface adjoining to the neck is provided with a number of ups and downs and the main body is made of silicone rubber, and a method of mounting a plane fastener onto the surface of a plate-like body made of silicone rubber used in the cervical orthoses or the like.

4 Claims, 3 Drawing Sheets

X-X Sectional View

Y-Y Sectional View

X-X Sectional View

Y-Y Sectional View

F I G. 4
(a)
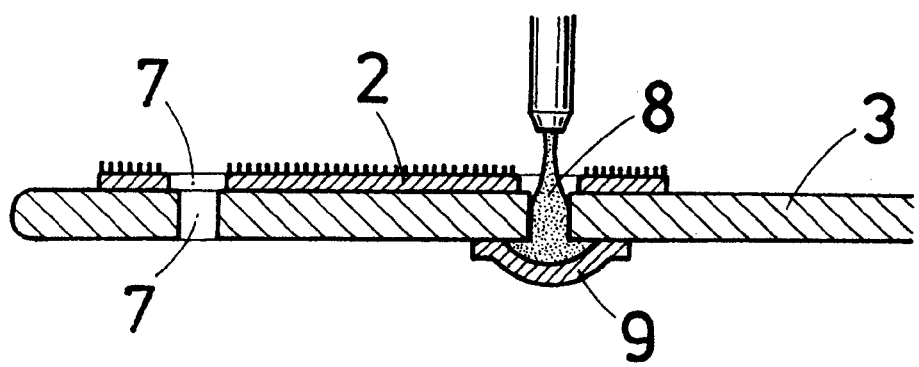
(b)
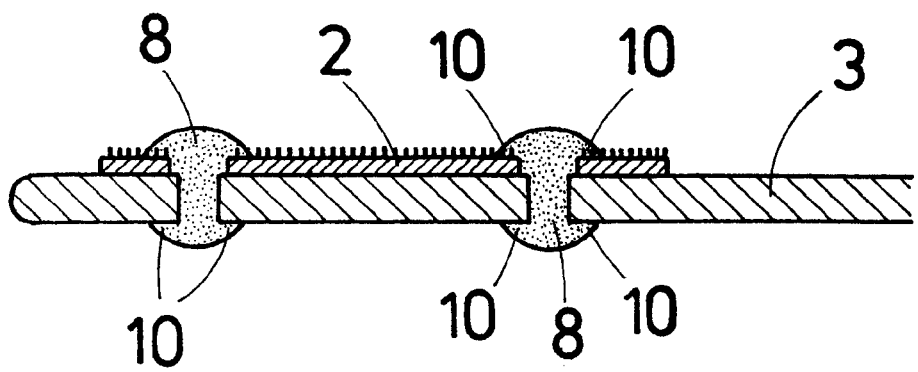

CERVICAL ORTHOSIS

BACKGROUND OF THE INVENTION

1. Field of the Invention

The present invention relates to a cervical orthosis, and more particularly to a structure of a cervical orthosis which is small, lightweight and easily fit on the neck and causes a comfortable feeling in use. The present invention does further relate to a method of mounting a fastener on objects.

2. Prior Art

Cervical vertebrae is the skeleton which supports the head having substantial weight, suspends the upper limbs and has a large movable range. Hence, it can be said that cervical vertebrae is the spine likely to undergo disorders (injuries, derangement, impairment, etc.) and to age. In fact, cervical vertebrae is known as a part apt to easily have disorders even from a minor car accident, and many people suffer from whiplash injury and its sequela or aftereffect.

Cervical vertebrae undergo also other disorders than the traumatopathy typically from the car accidents. In detail, it is known that spontaneous subluxation of atlanto-axial joint (generally anterior spontaneous subluxation) is seen in about 30% of cases of rheumatoid arthritis and causes not only local pain but also severe neurological disorders occasionally. The so-called conservative therapy using various cervical orthoses is usually applied to those disorders of cervical vertebrae. The cervical orthoses are classified on the basis of design generally into "Cervical (or orthopedic) collars", "Philadelphia collars", "Moulded cervical orthoses" and "Cervical orthoses with uprights", and a suitable type of orthosis is adopted in consideration of doctors' prescription on specific disorders as well as advantages and disadvantages of those cervical orthoses.

The cervical collars are low in control effect on such movements of cervical vertebrae as bending and extending forward and backward, rotating and lateral flexion but can be easily handled including adjustment of height and hardness. The cervical collars are more superior in keeping local temperatures and causing users to have a feeling of being firmly supported or of comfortableness in comparison with others at present. In addition, ready-made articles of the collars are available usually in four types LL, L, M and S and cheaply.

The Philadelphia collars are made of expanded polyethylene plate formed and characterized in a feeling of excellent comfortableness in use. The Philadelphia collars are enhanced in supporting effect for submaxilla and occiput of the head in comparison with the cervical collars, so that the collars restrain normal bending and extending movements of cervical vertebrae by about 30% but are said to be poor in restraining effect on movements as rotation and latexion.

The moulded cervical orthoses and the cervical orthoses with uprights are both extremely high in supporting effect for the head and in controlling effect on the movements of cervical vertebrae and are necessary to severe disorders, such as loss of supportability of skeleton due to deficiency or destruction of cervical vertebrae. (Usable for unstable vertebrae which require higher fixing effect than these orthoses is only the "skull traction".) The moulded cervical orthoses and the cervical orthoses with uprights are made of hard materials by moulding according to specifications of users to thereby he expensive and poor in comfortableness in use.

Various types or configurations of cervical orthoses have been hitherto proposed as above. An inherent clinical and therapeutic purpose of cervical orthoses is to mitigate pain and myopalmus caused by increment of movability of cervical vertebrae. However, excessive therapy or long use of the orthoses does or may cause muscle force lowering, myoatrophy, arthrogryposis, conditions turning worse occasionally, or psychogenic disorders originated from orthoses-dependency. Hence, orthoses which are mild in operation should be used at a minimum from necessity in a short term. Moreover, cases needing cervical orthoses superior in the control effect are rare practically. Most of the patients (whose disorders can be cured ambulantly and who wear orthoses in their daily life) may be caused to be conscious of their disorders by means of a prescribed light or mildly functional orthosis and lessen by themselves movement of their necks, thereby generally achieving the purpose of cure. Furthermore, easy attachment and removal of orthoses is an important requirement for selecting a a suitable orthosis in view of possible dactyl deformity or hypokinesis (diminished or slow movement) as seen in most of patients having cervical vertebrae disorders caused, for example, by chronic rheumatism. In this respect, the moulded cervical orthoses or the cervical orthoses with uprights should not be adopted.

Cervical orthoses to be prescribed or suitable for the patients (whose cervical vertebrae disorders are light or relatively mild) are those providing feelings of comfortableness and support in use but restraining excessive movement of cervical vertebrae without improved capacities of sustaining the weight of the head and stopping the extending and bending movement of cervical vertebrae.

Resulting from placing importance on these points and pursuing only the comfortableness in use and temperature-keeping efficiency, most of the conventional cervical orthoses were quite poor in the control effect.

Getting sticky with perspiration at the affected part upon use of cervical orthoses have been hitherto not considered. Some conventional cervical orthoses using sponge or urethane foam for providing "comfortableness" have caused aged persons, patients wishing to avoid skin irritation or those using the orthoses at night to feel uncomfortable. Under the circumstances, a cervical orthosis which has the control effect to some extent; does always provide excellent comfortableness in use; and is cheap to manufacture has been expected.

SUMMARY OF THE INVENTION

The inventor zealously made study the above problems and achieved the cervical orthosis according to the present invention which is characterized in that the cervical orthosis is applied around the neck corresponding to the cervical vertebrae and retained thereat to support and fix the same; is provided with a number of ups and downs at almost the whole of at least the surface close adjoining to the cervical vertebrae; and is made, at the main body, of silicone rubber.

In detail, the present invention is characterized in using silicone rubber as the material and having a number of ups and downs at least on the surface close adjoining to the neck. Silicone is an optimal material for the cervical orthoses since it is superior in oil and water resistance and has such properties of not likely to change in quality when long left on a region having perspiration; having an excellent contact with skin without a rash; and easily washable and dried to be kept sanitarily. Moreover, in use of cervical orthoses, convexed parts (among a lot of ups and downs provided on the surface close adjoining to the neck) suitably press and stimulate the neck to allow users to feel secure. Furthermore, the ups and downs feature in the form, for example, of a number of widthwise extending ridges may allow the orthosis to be easily bent and wound around and fixed on the neck while securing a supporting force for the weight of the head of users. Besides, the orthosis may be provided with the ups and downs also on the opposite surface to the side close adjoining to the neck to make contribution to the supporting effect for the head's weight.

Hardness of silicone rubber is not particularly limited and silicone rubber of a suitable hardness may be adopted since with orthoses having the same structural feature, high hardness of silicone rubber provides orthoses with high supporting force, in turn, high control effect while the comfortableness in use is deteriorated, and low hardness does to the contrary. It was appreciated from tests carried out by the inventor that non-expanded silicone rubber (hardness about 40–60 in JIS A [Shore A] rubber hardness test) when set to be about 5 mm in (average) thickness is enough for securing sufficient strength to support cervical vertebrae, thereby being an ideal material for a lightweight soft orthosis.

The cervical orthosis according to the present invention is basically in the form of a narrow plate (capable of being deflected) to lie flat when not subjected to a force. In consideration of use of the orthosis to be wound around the cervical vertebrae part, the orthosis may be moulded into a shape as kept cylindrically bent when unaffected. The shape allows easy attachment to the neck and a less force required for retaining both ends of the orthosis after winding around the neck. Means for retaining both ends of the orthosis may preferably employ a "plane (or planar) fastener" enabling fine adjustment of retaining points without use of metal parts.

Mounting and fixing the plane fastener on the orthosis body is not so easy. The orthosis body is made of silicone rubber which has the advantages as excellent contact with skin and being sanitary as foregoing while having such defects as being fragile and poor in adhesiveness to easily peel off. Mounting the plane fastner on silicone rubber is conventionally only by adhesion (but not by stitching due to the fragility) and there was a fear of the fastener's peeling off from the orthosis body after repeated operation of fastening.

In this respect, the inventor has herein also proposed another invention, a method of mounting the plane fastener on the plate-like body of silicone rubber, wherein the plate-like body and the plane fastener are each provided with a plurality of through bores, which through bores are aligned when the plane fastener is placed in position on the plate-like body, and after placing the plane fasteners in position on the plate-like body melted silicone is applied in the aligned through bores to be solidified in the form of rivets, or silicone rubber formed in a shape having a projecting part like nail heads, in place of the melted silicone, is inserted into the aligned through bores to be melted at one of the projecting parts and solidified again to provide or re-form a projecting part.

The plate-like body made of silicone rubber may cover or include also all of the same parts comprising a belt portion made of silicone rubber used in lumbar vertebrae orthoses, kneejoint orthoses, etc.

To solidify the melted silicone into the rivet-like shape, the inventor adopted such way that a receiving means is set to abut against upper or lower side of the disposed plane fastener and orthosis body and receive the melted silicone from the upper side to form the projecting part first at the lower side (followed by making another projecting part at the upper side after completion of feeding the melted silicone). Formation of the projecting parts may be in a separate manner.

BRIEF DESCRIPTION OF THE DRAWINGS

FIGS. 4(a) and 4(b) are schematic sectional views showing an example of a method of mounting the plane fastener according to the present invention.

DETAILED DESCRIPTION OF THE INVENTION

Embodiments

Figure 1:
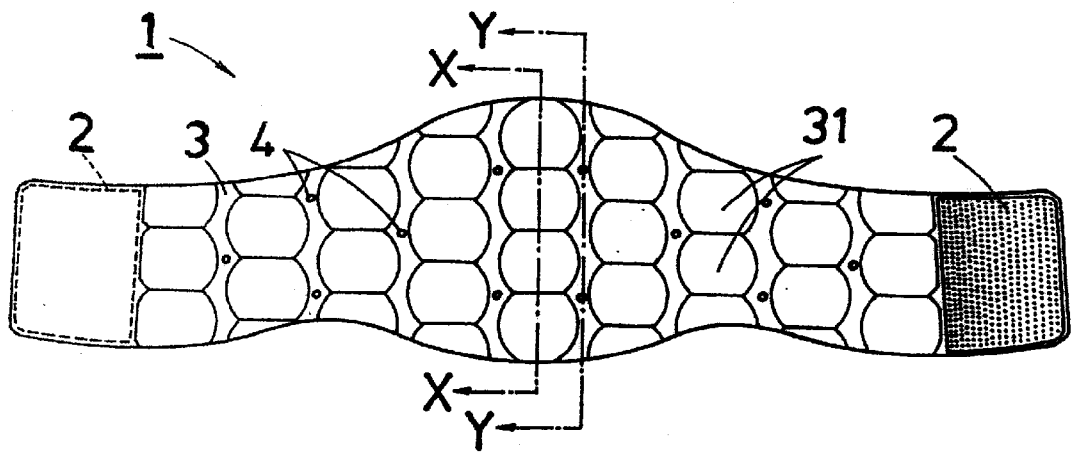
FIG. 1 is a plan view with two sectional views showing an example of a cervical orthosis according to the present invention.
Figure 1:
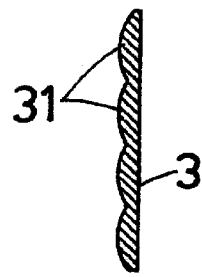
Figure 1:
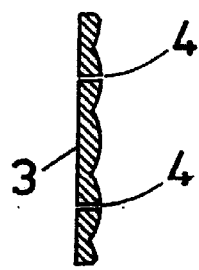

Next, the present invention will be further detailed with referring to specific examples of the invention shown in the drawings.

FIG. 1 shows an example of a cervical orthosis 1 according to the present invention (called hereunder "the orthosis 1"). The orthosis 1 in this example is a plate-like shaped member (body) larger in "width" at the middle as clearly seen in the direction of the line X—X in FIG. 1 and having a plane fastener 2 adhered on each end (the left and right ends in the drawing). The fasteners 2 are not placed on the same surface, one (the righthand one in FIG. 1) on the front side and the other on the rear side. The orthosis 1 comprises a main body 3 and the plane fasteners 2 without any other members.

The main body 3 is made of non-expanded (or non-foamed) type of silicone rubber (hardness 45 in JIS A [Shore A] rubber hardness test). The main body 3 is not flat on the surface but has a number of convex projections 31 on both of front and rear sides except an area for mounting the plane fasteners 2. Small bores 4 are bored in the main body 3 to extend through the same for ventilation. The configuration of the convex projections 31 may be in the form of a number of sections of spheres arranged or layed on a plane as overlapping one another in the direction of width (it is actually an integrally formed product). This shape of the surface provides that a force required for bending to decrease a distance in the direction of width (between the upper and lower ends in the drawing) is larger than that decreasing a distance in the longitudinal direction (between the lefthand end and the righthand end in the drawing). The projections 31 on the front and rear sides of the main body 3 are respectively shifted in position in the longitudinal direction as seen in the sectional views taken in the lines X—X and Y—Y in FIG. 1 wherein the Y—Y portion (a bottom area on the front side) corresponds to a crest on the rear side. Hence, the bottom areas not having the projections 31 do not align with one another on the front and rear sides of the main body 3, so that the main body 3 does not have an extremely thin part, secures strength and provides a gentle curving shape of the main body 3 when wound around the neck.

Figure 2:
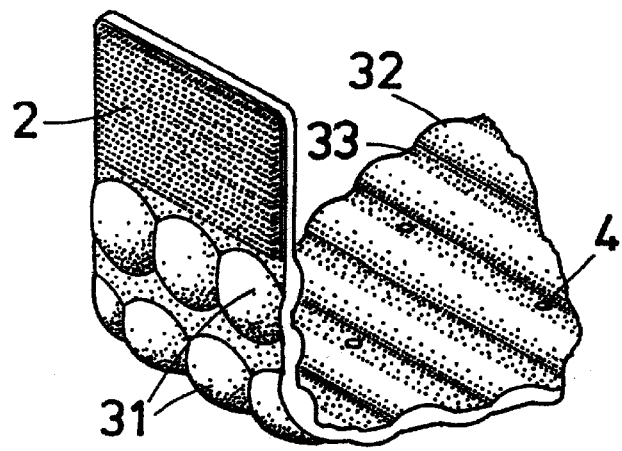
FIG. 2 is a schematic perspective view showing another example of the ups and downs feature on the surface of the orthosis main body.

FIG. 2 illustrates another example of ups and downs feature provided on the main body 3. On the front surface of the main body 3 (opposite to the side adjoining to the neck) is formed a gentle ups and downs configuration having a plurality of sets of ridges 32 and grooves 33 extending parallel to each other in the direction of width of the main body 3. The main body 3 has the same or similar projections 31 as of FIG. 1 on the rear surface. In use of the orthosis those ridges or convex parts press and stimulate the neck to cause patients or users to feel comfortable.

Figure 3:
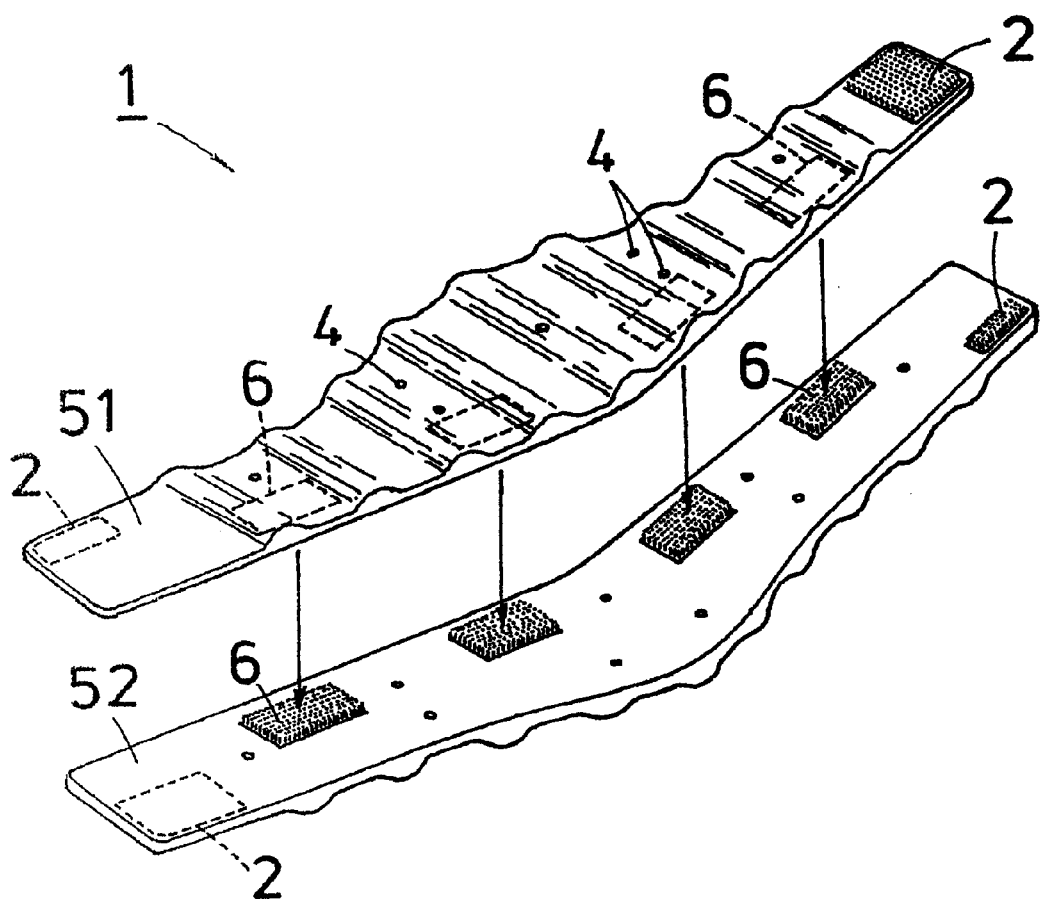
FIG. 3 is a schematic perspective view showing a further example of a cervical orthosis according to the present invention.

FIG. 3 shows a further example of the cervical orthosis 1 according to the present invention comprising a combination of main body halves 51 and 52 provided by widthwise dividing the main body. The main body halves 51 and 52 are retained to each other with a plurality of plane fasteners 6 arranged at a predetermined interval in the longitudinal direction, thereby enabling fine adjustment of width (i.e., height in use of the orthosis). In this example, the main body halve 51 has ridges 32 and grooves 33 on the upper surface and another main body half 52 has on the lower surface the projections 31 as shown in FIG. 1 but not clearly seen in FIG. 3. The main body halves 51 and 52 do not have the ups and downs feature to be flat on their opposing surfaces, and there may be provided the ups and downs configuration (not shown) in a style not hindering the foregoing adjustment of width (height in use). Furthermore, the orthosis 1 in this example does not require any skill in use, i.e., attaching and detaching the orthosis, and users (patients) may merely wind (and fix) around their necks the orthosis 1, i.e., the main body halves 51 and 52 retained to and overlapping with each other as defining a specific width (height in use) prescribed or set by specialists, doctors or the like. In case that the cervical orthosis according to the present invention having the above structure are prepared as ready-made articles, a mere small variation of articles is enough for covering almost all cases (patients) and enables manufacturing at a low cost.

FIG. 4 schematically shows the method of mounting the plane fastener 2 on the main body 3, exemplifying an intermediate step in the course of process. The main body 3 and plane fasteners 2 are bored to have through bores 7 previously or upon mounting the plane fasteners on the main body. Melted silicone 8 is fed into the bores 7 (FIG. 4(*a*)).

A mould 9 (for forming the projecting part and also serving as prevention of leakage of melted silicone 8) is set at one side of the arranged plane fastener and main body (opposite to the side where the melted silicone 8 is fed) to solidify the melted silicone 8. A mould (not shown) in the same or separate shape of the mould 9 may be set at that side of feeding the melted silicone to form the projecting part.

The melted silicone 8 when completely solidified does, like rivets capable of being deflected and as seen in FIG. 4(*b*), sandwich between the upper and lower projecting parts 10 the main body 3 and plane fastener 2 to hold them integrally, whereby preventing the plane fastener 2 from peeling off from the main body 3 even when the main body 3 is made of silicone.

Size and shape of the projecting parts 10 and size and number of the through bores 7 may be selected properly in accordance with required strength or other conditions.

Effect of the Invention

As seen from the above, the present invention is a cervical orthosis to be wound onto the neck around the cervical vertebrae part and retained to support and fix the cervical vertebrae and characterized in that almost the whole of at least the surface adjoining to the neck is provided with a number of ups and downs and the main body is made of silicone rubber. The invention does also relate to a method of mounting a plane fastener onto the surface of a plate-like body made of silicone rubber used in the cervical orthoses or the like wherein a plurality of through bores are provided on the plate-like body and the plane fastener and are aligned with one another when the plane fastener is placed in position on the plate-like body, and after placing the plane fastener on the plate-like body melted slicone is fed into the aligned through bores to be solidified in the form of rivets, or silicone rubber having a projecting part like a nail head in place of the melted silicone is inserted into the aligned through bores on the plate-like body and plane fastener followed by melting the projecting part at one end of the inserted silicone rubber and solidifying again the same to re-form the projecting part. The present invention is quite highly advanced to have the following various effects.

(1) The orthosis is flexible without using metallic members and is non-bulky, lightweight and excellent in comfortableness in use.

(2) The orthosis is made of silicone rubber superior in oil resistance and water resistance. Users wearing the orthosis may take a bath or a shower. Besides, silicone rubber is not likely to deteriorate and the orthosis can long keep an initial high level of the effects.

(3) The orthosis uses silicone which has an excellent contact with skin without a rash after long contacting.

(4) The orthosis has the ups and downs on the surface of the main body and the ridges or convex projections press and stimulate the neck in use of the orthosis, thereby providing an effect of massotherapy and a feeling of security that users can always feel or recognize as the neck being protected by the orthosis.

(5) According to the present invention, a plate-like member (body) made of silicone rubber (from which a plane fastener is known to be likely to peel off) can mount thereon the plane fastener without peeling off.

What we claimed is:

1. A cervical orthosis arranged to be applied around the neck of a user corresponding to cervical vertebrae and retained thereat for supporting and fixing the same, having a main body of non-expanded silicone rubber, provided with a number of convex projections in the form of a number of sections of spheres, at almost the whole of at least the surface closely adjoining to the neck.

2. A cervical orthosis as set forth in claim 1, wherein the main body comprises a combination of two main-body halves to be retained to each other as partially over-lapping widthwise for adjustment of width or height of the cervical orthosis in use.

3. A cervical orthosis as set forth in claim 1, wherein said main body has a width and said convex projections are arranged on a plane as overlapping one another in the direction of said width.

4. A method of mounting a plane fastener on a body made of silicone rubber wherein the body and the plane fastener are each provided with a plurality of through bores, which through bores are aligned when the plane fastener is placed in position on the body, and, after placing the plane fasteners in position on the body, melted silicone is applied in the aligned through bores to be solidified in the form of rivets, or silicone rubber in a shape having a projecting part nail heads in place of the melted silicone is inserted into the aligned through bores to be melted at one of the projecting parts and solidified again to provide or re-form the projecting part.

\* \* \* \* \*